(12) United States Patent
Schmidt et al.

(10) Patent No.: US 10,842,993 B2
(45) Date of Patent: Nov. 24, 2020

(54) LEADLESS CARDIAC PACING DEVICES

(71) Applicant: Cardiac Pacemakers, Inc., St. Paul, MN (US)

(72) Inventors: Brian L. Schmidt, White Bear Lake, MN (US); Benjamin J. Haasl, Forest Lake, MN (US); Dana Sachs, Pine City, MN (US); Arthur J. Foster, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 818 days.

(21) Appl. No.: 14/452,607

(22) Filed: Aug. 6, 2014

(65) Prior Publication Data

US 2015/0051612 A1    Feb. 19, 2015

Related U.S. Application Data

(60) Provisional application No. 61/866,813, filed on Aug. 16, 2013.

(51) Int. Cl.
*A61N 1/05* (2006.01)
*A61N 1/375* (2006.01)
*A61N 1/372* (2006.01)

(52) U.S. Cl.
CPC ......... *A61N 1/0573* (2013.01); *A61N 1/3756* (2013.01); *A61N 1/37205* (2013.01); *A61N 2001/058* (2013.01)

(58) Field of Classification Search
CPC .... A61N 1/3756; A61N 1/0573; A61N 1/362; A61N 1/375; A61N 1/057; A61N 1/056; A61N 1/0587; A61N 1/059; A61N 1/05; A61N 1/37205; A61N 1/0578; A61N 1/058; A61N 2001/058; A61N 2001/0578; A61N 2001/0585; A61N 2001/0558; A61B 17/3468; A61F 2002/011; A61F 2/95;

(Continued)

(56) References Cited

U.S. PATENT DOCUMENTS

| 721,869 A | 3/1903 | Dunning |
| 3,717,151 A | 2/1973 | Collett |

(Continued)

FOREIGN PATENT DOCUMENTS

| CA | 1003904 A1 | 1/1977 |
| DE | 2053919 A1 | 5/1972 |

(Continued)

OTHER PUBLICATIONS

Spickler, et al. "Totally Self-Contained Intracardiac Pacemaker" J. Electrocardiology, vol. 3, Nos. 3 & 4, pp. 325-331 (1970).

*Primary Examiner* — Elizabeth Houston
*Assistant Examiner* — Socrates L Boutsikaris
(74) *Attorney, Agent, or Firm* — Seager, Tufte & Wickhem LLP

(57) ABSTRACT

Implantable leadless pacing devices and medical device systems including an implantable leadless pacing device are disclosed. An example implantable leadless pacing device may include a pacing capsule. The pacing capsule may include a housing. The housing may have a proximal region and a distal region. A first electrode may be disposed along the distal region. An anchoring member may be coupled to the distal region. One or more anti-rotation members may be fixedly attached to the distal region.

16 Claims, 11 Drawing Sheets

(58) Field of Classification Search
CPC .......... A61F 2/966; A61F 2/2466; A61M 2025/0681; A61M 2025/006; A61M 2025/0062; A61M 2025/0161; A61M 25/0074; A61M 25/008; A61M 25/0141
USPC .............................. 606/129; 607/36; 33/129
See application file for complete search history.

(56) References Cited

U.S. PATENT DOCUMENTS

| | | |
|---|---|---|
| 3,754,555 A | 8/1973 | Schmitt |
| 3,814,104 A | 6/1974 | Irnich et al. |
| 3,835,864 A | 9/1974 | Rasor et al. |
| 3,902,501 A | 9/1975 | Citron et al. |
| 3,943,936 A | 3/1976 | Rasor |
| 3,971,364 A | 7/1976 | Fletcher et al. |
| 3,976,082 A | 8/1976 | Schmitt |
| 4,103,690 A | 8/1978 | Harris |
| 4,112,952 A | 9/1978 | Thomas et al. |
| 4,269,198 A | 5/1981 | Stokes |
| 4,280,512 A | 7/1981 | Karr |
| 4,301,815 A | 11/1981 | Doring |
| 4,402,328 A | 9/1983 | Doring |
| 4,409,994 A | 10/1983 | Doring |
| 4,502,492 A | 3/1985 | Bornzin |
| 4,662,382 A | 5/1987 | Sluetz et al. |
| 4,898,577 A | 2/1990 | Badger et al. |
| 4,913,164 A | 4/1990 | Greene et al. |
| 5,003,990 A | 4/1991 | Osypka |
| 5,057,114 A | 10/1991 | Wittich et al. |
| 5,129,749 A | 7/1992 | Sato |
| 5,171,233 A | 12/1992 | Amplatz et al. |
| 5,193,540 A | 3/1993 | Schulman et al. |
| 5,257,634 A | 11/1993 | Kroll |
| 5,282,845 A | 2/1994 | Bush et al. |
| 5,300,107 A | 4/1994 | Stokes et al. |
| 5,318,528 A | 6/1994 | Heaven et al. |
| 5,336,253 A | 8/1994 | Gordon et al. |
| 5,405,367 A | 4/1995 | Schulman et al. |
| 5,405,374 A | 4/1995 | Stein |
| 5,411,535 A | 5/1995 | Fujii et al. |
| 5,425,756 A | 6/1995 | Heil et al. |
| 5,443,492 A | 8/1995 | Stokes et al. |
| 5,492,119 A | 2/1996 | Abrams |
| 5,522,875 A | 6/1996 | Gates et al. |
| 5,522,876 A | 6/1996 | Rusink |
| 5,545,201 A | 8/1996 | Helland et al. |
| 5,545,206 A | 8/1996 | Carson |
| 5,562,723 A | 10/1996 | Rugland et al. |
| 5,575,814 A | 11/1996 | Giele et al. |
| 5,578,068 A | 11/1996 | Laske et al. |
| 5,697,936 A | 12/1997 | Shipko et al. |
| 5,716,390 A | 2/1998 | Li |
| 5,716,391 A | 2/1998 | Grandjean |
| 5,755,764 A | 5/1998 | Schroeppel |
| 5,776,178 A | 7/1998 | Pohndorf et al. |
| 5,807,399 A | 9/1998 | Laske et al. |
| 5,837,006 A | 11/1998 | Ocel et al. |
| 5,837,007 A | 11/1998 | Altman et al. |
| 5,851,226 A | 12/1998 | Skubitz et al. |
| 5,871,531 A | 2/1999 | Struble |
| 5,908,381 A | 6/1999 | Aznoian et al. |
| 5,908,447 A | 6/1999 | Schroeppel et al. |
| 6,041,258 A | 3/2000 | Cigaina et al. |
| 6,055,457 A | 4/2000 | Bonner |
| 6,074,401 A | 6/2000 | Gardnier et al. |
| 6,078,840 A | 6/2000 | Stokes |
| 6,093,177 A | 7/2000 | Javier et al. |
| 6,129,749 A | 10/2000 | Bartig et al. |
| 6,132,456 A | 10/2000 | Sommer et al. |
| 6,181,973 B1 | 1/2001 | Ceron et al. |
| 6,188,932 B1 | 2/2001 | Lindegren |
| 6,240,322 B1 | 5/2001 | Peterfeso et al. |
| 6,251,104 B1 | 6/2001 | Kesten et al. |
| 6,290,719 B1 | 9/2001 | Garberoglio |
| 6,321,124 B1 | 11/2001 | Cigaina |
| 6,322,548 B1 | 11/2001 | Payne et al. |
| RE37,463 E | 12/2001 | Altman |
| 6,358,256 B1 | 3/2002 | Reinhardt |
| 6,363,938 B2 | 4/2002 | Saadat et al. |
| 6,381,495 B1 | 4/2002 | Jenkins |
| 6,381,500 B1 | 4/2002 | Fischer, Sr. |
| 6,408,214 B1 | 6/2002 | Williams et al. |
| 6,458,145 B1 | 10/2002 | Ravenscroft et al. |
| 6,477,423 B1 | 11/2002 | Jenkins |
| 6,500,182 B2 | 12/2002 | Foster |
| 6,510,332 B1 | 1/2003 | Greenstein |
| 6,510,345 B1 | 1/2003 | Van Bentem |
| 6,522,915 B1 | 2/2003 | Ceballos et al. |
| 6,572,587 B2 | 6/2003 | Lerman et al. |
| 6,582,441 B1 | 6/2003 | He et al. |
| 6,592,581 B2 | 7/2003 | Bowe |
| 6,623,518 B2 | 9/2003 | Thompson et al. |
| 6,626,915 B2 | 9/2003 | Leveillee |
| 6,638,268 B2 | 10/2003 | Niazi |
| 6,684,109 B1 | 1/2004 | Osypka |
| 6,711,443 B2 | 3/2004 | Osypka |
| 6,743,240 B2 | 6/2004 | Smith et al. |
| 6,755,812 B2 | 6/2004 | Peterson et al. |
| 6,909,920 B2 | 6/2005 | Lokhoff et al. |
| 6,944,507 B2 | 9/2005 | Froberg et al. |
| 6,953,454 B2 | 10/2005 | Peterson et al. |
| 7,027,876 B2 | 4/2006 | Casavant et al. |
| 7,082,335 B2 | 7/2006 | Klein et al. |
| 7,085,606 B2 | 8/2006 | Flach et al. |
| 7,092,765 B2 | 8/2006 | Geske et al. |
| 7,092,766 B1 | 8/2006 | Salys et al. |
| 7,120,504 B2 | 10/2006 | Osypka |
| 7,149,587 B2 | 12/2006 | Wardle et al. |
| 7,158,838 B2 | 1/2007 | Seifert et al. |
| 7,162,310 B2 | 1/2007 | Doan |
| 7,181,288 B1 | 2/2007 | Rezai et al. |
| 7,187,982 B2 | 3/2007 | Seifert et al. |
| 7,200,437 B1 | 4/2007 | Nabutovsky et al. |
| 7,212,869 B2 | 5/2007 | Wahlstrom et al. |
| 7,229,415 B2 | 6/2007 | Schwartz |
| 7,251,532 B2 | 7/2007 | Hess et al. |
| 7,289,853 B1 | 10/2007 | Campbell et al. |
| 7,313,445 B2 | 12/2007 | McVenes et al. |
| 7,326,231 B2 | 2/2008 | Phillips et al. |
| 7,328,071 B1 | 2/2008 | Stehr et al. |
| 7,383,091 B1 | 6/2008 | Chitre et al. |
| 7,450,999 B1 | 11/2008 | Karicherla et al. |
| 7,462,184 B2 | 12/2008 | Worley et al. |
| 7,463,933 B2 | 12/2008 | Wahlstrom et al. |
| 7,499,758 B2 | 3/2009 | Cates et al. |
| 7,509,169 B2 | 3/2009 | Eigler et al. |
| 7,515,971 B1 | 4/2009 | Doan |
| 7,532,939 B2 | 5/2009 | Sommer et al. |
| 7,558,631 B2 | 7/2009 | Cowan et al. |
| 7,634,319 B2 | 12/2009 | Schneider et al. |
| 7,647,109 B2 | 1/2010 | Hastings et al. |
| 7,657,325 B2 | 2/2010 | Williams |
| 7,678,128 B2 | 3/2010 | Boyle et al. |
| 7,717,899 B2 | 5/2010 | Bowe et al. |
| 7,731,655 B2 | 6/2010 | Smith et al. |
| 7,734,343 B2 | 6/2010 | Ransbury et al. |
| 7,740,640 B2 | 6/2010 | Ginn |
| 7,785,264 B2 | 8/2010 | Hettrick et al. |
| 7,799,037 B1 | 9/2010 | He et al. |
| 7,801,624 B1 | 9/2010 | Flannery et al. |
| 7,835,801 B1 | 11/2010 | Sundararajan et al. |
| 7,840,281 B2 | 11/2010 | Kveen et al. |
| 7,840,283 B1 | 11/2010 | Bush et al. |
| 7,860,580 B2 | 12/2010 | Falk et al. |
| 7,875,049 B2 | 1/2011 | Eversull et al. |
| 7,890,186 B2 | 2/2011 | Wardle et al. |
| 7,904,179 B2 | 3/2011 | Ruffen et al. |
| 7,920,928 B1 | 4/2011 | Yang et al. |
| 7,993,351 B2 | 8/2011 | Worley et al. |
| 8,010,209 B2 | 8/2011 | Jacobson |
| 8,036,757 B2 | 10/2011 | Worley |
| 8,057,486 B2 | 11/2011 | Hansen |
| 8,082,035 B2 | 12/2011 | Glukhovsky |
| 8,103,361 B2 | 1/2012 | Moser |

(56) References Cited

U.S. PATENT DOCUMENTS

| | | | |
|---|---|---|---|
| 8,108,054 B2 | 1/2012 | Helland | |
| 8,142,347 B2 | 3/2012 | Griego et al. | |
| 8,160,722 B2 | 4/2012 | Ruffen et al. | |
| 8,185,213 B2 | 5/2012 | Kveen et al. | |
| 8,219,213 B2 | 7/2012 | Sommer et al. | |
| 8,233,994 B2 | 7/2012 | Sommer et al. | |
| 8,252,019 B2 | 8/2012 | Fleming, III | |
| 8,295,939 B2 | 10/2012 | Jacobson | |
| 8,313,445 B2 | 11/2012 | Mishima et al. | |
| 8,352,025 B2 | 1/2013 | Jacobson | |
| 8,352,028 B2 | 1/2013 | Wenger | |
| 8,364,277 B2 | 1/2013 | Glukhovsky | |
| 8,364,280 B2 | 1/2013 | Marnfeldt et al. | |
| 8,406,900 B2 | 3/2013 | Barlov et al. | |
| 8,406,901 B2 | 3/2013 | Starkebaum et al. | |
| 8,428,750 B2 | 4/2013 | Kolberg | |
| 8,452,420 B2 | 5/2013 | Flach et al. | |
| 8,478,431 B2 | 7/2013 | Griswold et al. | |
| 8,489,189 B2 | 7/2013 | Tronnes | |
| 8,494,650 B2 | 7/2013 | Glukhovsky et al. | |
| 8,504,156 B2 | 8/2013 | Bonner et al. | |
| 8,518,060 B2 | 8/2013 | Jelich et al. | |
| 8,527,068 B2 | 9/2013 | Ostroff | |
| 8,532,790 B2 | 9/2013 | Griswold | |
| 8,548,605 B2 | 10/2013 | Ollivier | |
| 8,565,897 B2 | 10/2013 | Regnier et al. | |
| 8,615,310 B2 | 12/2013 | Khairkhahan et al. | |
| 8,634,912 B2 | 1/2014 | Bornzin et al. | |
| 8,670,842 B1 | 3/2014 | Bornzin et al. | |
| 8,721,587 B2 | 5/2014 | Berthiaume et al. | |
| 8,727,996 B2 | 5/2014 | Allan et al. | |
| 8,758,365 B2 | 6/2014 | Bonner et al. | |
| 2002/0077556 A1 | 6/2002 | Schwartz | |
| 2003/0004537 A1 | 1/2003 | Boyle et al. | |
| 2004/0176797 A1 | 9/2004 | Opolski | |
| 2005/0090890 A1 | 4/2005 | Wu et al. | |
| 2005/0267555 A1 | 12/2005 | Marnfeldt et al. | |
| 2006/0247753 A1 | 11/2006 | Wenger et al. | |
| 2007/0135883 A1 | 6/2007 | Drasler et al. | |
| 2007/0150037 A1 | 6/2007 | Hastings et al. | |
| 2007/0150038 A1 | 6/2007 | Hastings et al. | |
| 2007/0233218 A1 | 10/2007 | Kolberg | |
| 2007/0239248 A1 | 10/2007 | Hastings et al. | |
| 2007/0255376 A1 | 11/2007 | Michels et al. | |
| 2007/0276444 A1 | 11/2007 | Gelbart | |
| 2007/0293904 A1 | 12/2007 | Gelbart | |
| 2008/0021532 A1 | 1/2008 | Kveen et al. | |
| 2008/0109054 A1* | 5/2008 | Hastings | A61N 1/0587 607/127 |
| 2009/0082828 A1* | 3/2009 | Ostroff | A61N 1/3756 607/36 |
| 2009/0281605 A1 | 11/2009 | Marnfeldt et al. | |
| 2010/0114280 A1* | 5/2010 | Hill | A61N 1/0573 607/116 |
| 2010/0198288 A1 | 8/2010 | Ostroff | |
| 2010/0234931 A1* | 9/2010 | Jarl | A61N 1/0573 607/149 |
| 2011/0034939 A1 | 2/2011 | Kveen et al. | |
| 2011/0112548 A1 | 5/2011 | Fifer et al. | |
| 2011/0125163 A1 | 5/2011 | Rutten et al. | |
| 2011/0190785 A1 | 8/2011 | Gerber et al. | |
| 2011/0190786 A1 | 8/2011 | Gerber et al. | |
| 2011/0208260 A1 | 8/2011 | Jacobson | |
| 2011/0237967 A1 | 9/2011 | Moore et al. | |
| 2011/0270339 A1 | 11/2011 | Murray, III et al. | |
| 2011/0270340 A1 | 11/2011 | Pellegrini et al. | |
| 2011/0282423 A1 | 11/2011 | Jacobson | |
| 2011/0307043 A1 | 12/2011 | Ollivier | |
| 2012/0078322 A1 | 3/2012 | Dal Molin et al. | |
| 2012/0078336 A1 | 3/2012 | Helland | |
| 2012/0095539 A1 | 4/2012 | Khairkhahan et al. | |
| 2012/0109002 A1 | 5/2012 | Mothilal et al. | |
| 2012/0109079 A1 | 5/2012 | Asleson et al. | |
| 2012/0109148 A1 | 5/2012 | Bonner et al. | |
| 2012/0109149 A1 | 5/2012 | Bonner et al. | |
| 2012/0116489 A1* | 5/2012 | Khairkhahan | A61N 1/37518 607/127 |
| 2012/0158111 A1 | 6/2012 | Khairkhahan et al. | |
| 2012/0165827 A1 | 6/2012 | Khairkhahan et al. | |
| 2012/0172690 A1 | 7/2012 | Anderson et al. | |
| 2012/0172891 A1 | 7/2012 | Lee | |
| 2012/0172892 A1 | 7/2012 | Grubac et al. | |
| 2012/0197373 A1 | 8/2012 | Khairkhahan et al. | |
| 2012/0232565 A1 | 9/2012 | Kveen et al. | |
| 2012/0271134 A1 | 10/2012 | Allan et al. | |
| 2012/0330392 A1 | 12/2012 | Regnier et al. | |
| 2013/0006261 A1 | 1/2013 | Lampropoulos et al. | |
| 2013/0006262 A1 | 1/2013 | Lampropoulos et al. | |
| 2013/0012925 A1 | 1/2013 | Berthiaume et al. | |
| 2013/0035636 A1 | 2/2013 | Beasley et al. | |
| 2013/0035748 A1 | 2/2013 | Bonner et al. | |
| 2013/0053921 A1 | 2/2013 | Bonner et al. | |
| 2013/0079798 A1 | 3/2013 | Tran et al. | |
| 2013/0079861 A1 | 3/2013 | Reinert et al. | |
| 2013/0103047 A1 | 4/2013 | Steingisser et al. | |
| 2013/0103049 A1 | 4/2013 | Medtronic | |
| 2013/0116741 A1 | 5/2013 | Bornzin et al. | |
| 2013/0123875 A1 | 5/2013 | Varady et al. | |
| 2013/0131591 A1 | 5/2013 | Berthiaume et al. | |
| 2013/0131693 A1 | 5/2013 | Berthiaume et al. | |
| 2013/0253342 A1 | 9/2013 | Griswold et al. | |
| 2013/0253343 A1 | 9/2013 | Waldhauser et al. | |
| 2013/0253344 A1 | 9/2013 | Griswold et al. | |
| 2013/0253345 A1 | 9/2013 | Griswold et al. | |
| 2013/0253346 A1 | 9/2013 | Griswold et al. | |
| 2013/0253347 A1 | 9/2013 | Griswold et al. | |
| 2013/0296957 A1 | 11/2013 | Tronnes | |
| 2014/0058494 A1 | 2/2014 | Ostroff et al. | |
| 2014/0074114 A1 | 3/2014 | Khairkhahan et al. | |
| 2014/0148815 A1 | 5/2014 | Wenzel et al. | |
| 2014/0180306 A1 | 6/2014 | Grubac et al. | |
| 2014/0303704 A1* | 10/2014 | Suwito | A61N 1/059 607/119 |
| 2014/0324145 A1* | 10/2014 | Eggen | A61N 1/0573 607/119 |

FOREIGN PATENT DOCUMENTS

| | | |
|---|---|---|
| EP | 779080 B1 | 5/2003 |
| JP | 05245215 A | 9/1993 |
| WO | 03032807 A2 | 4/2003 |
| WO | 2009039400 A1 | 3/2009 |
| WO | 2012092067 A1 | 7/2012 |
| WO | 2012092074 A1 | 7/2012 |

* cited by examiner

FIG. 2A
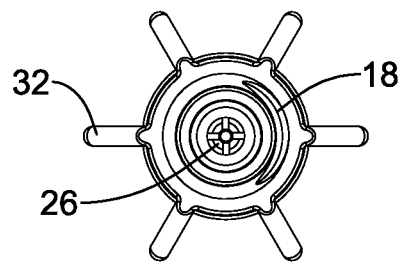
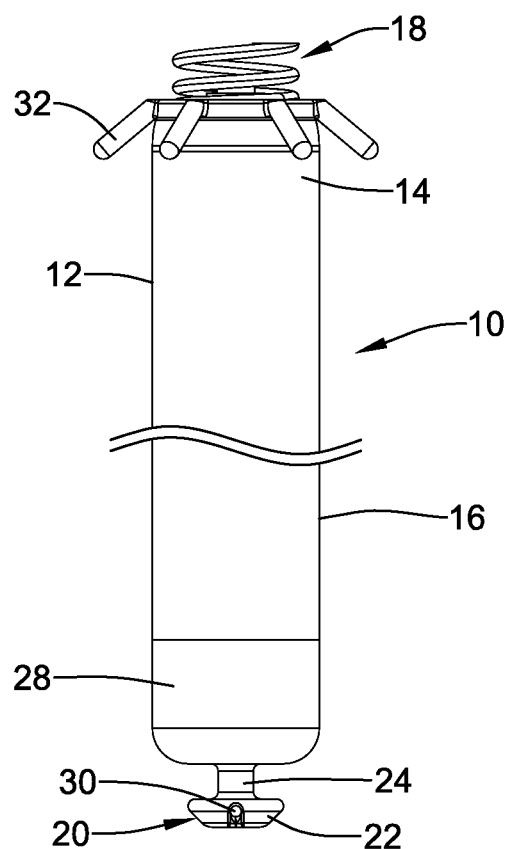
FIG. 2
FIG. 2B
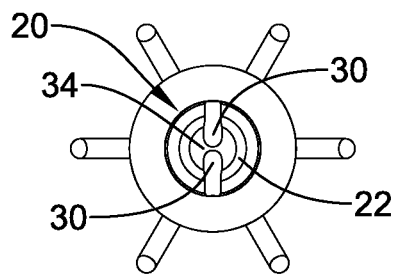

FIG. 3A
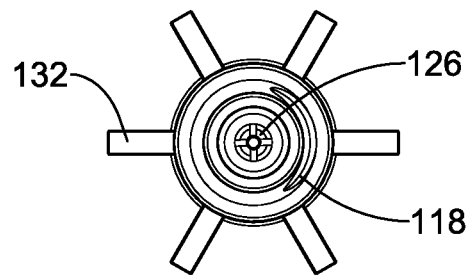
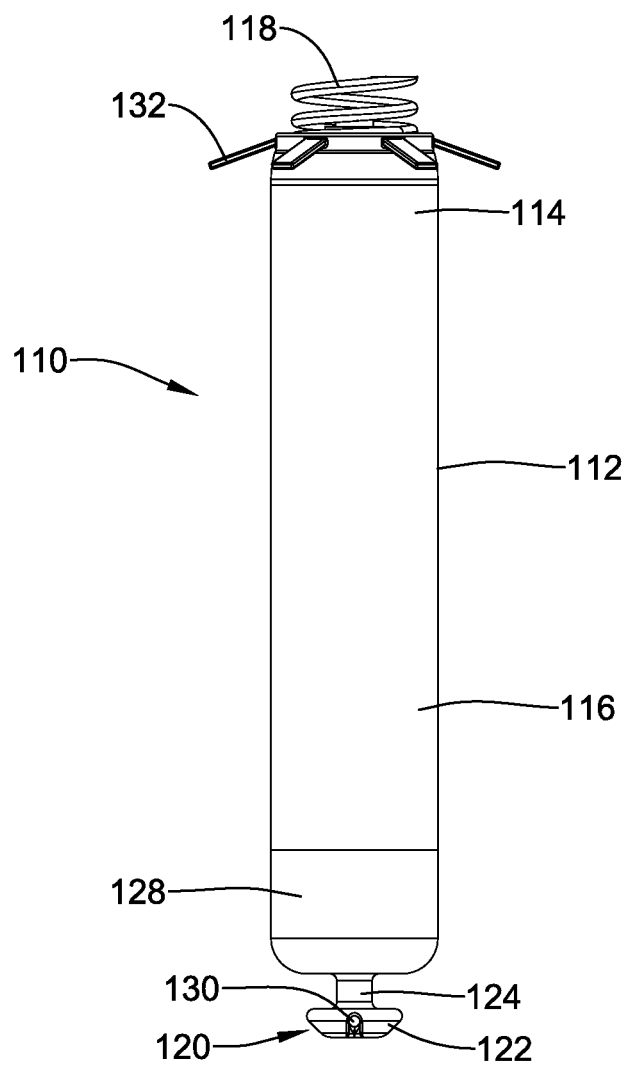
FIG. 3

FIG. 4A
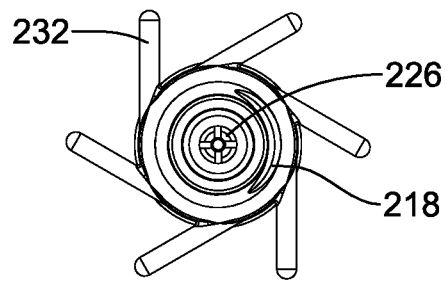
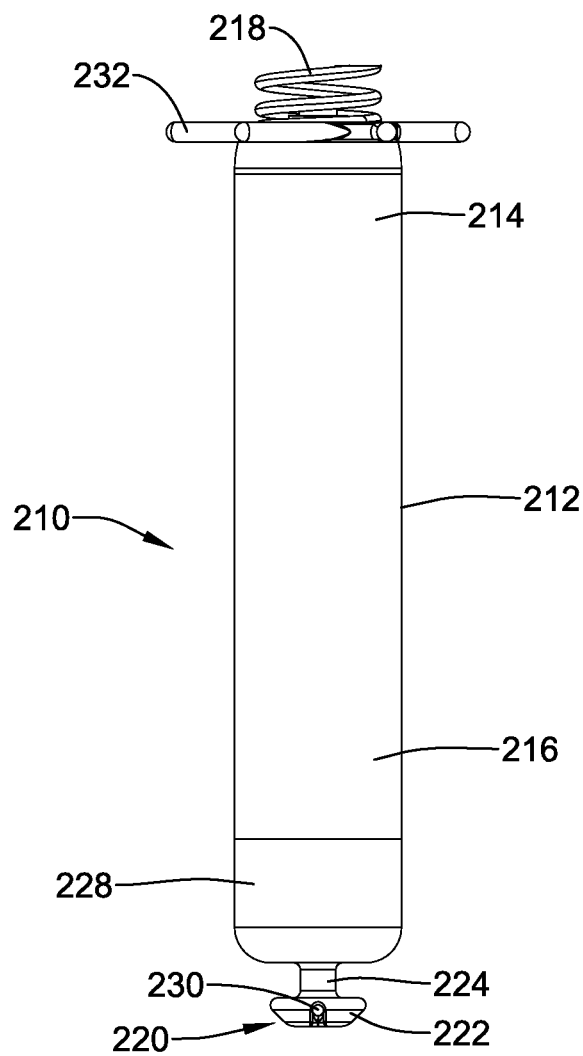
FIG. 4

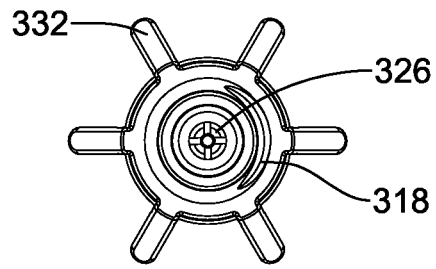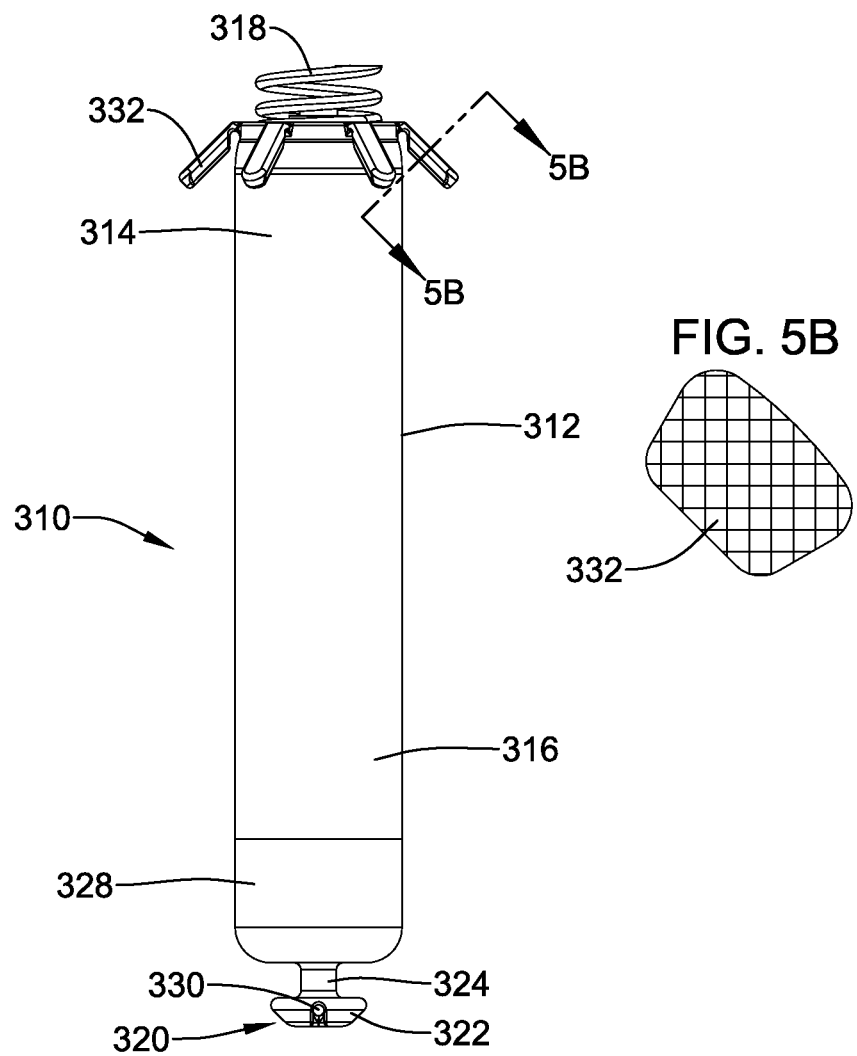

FIG. 6A
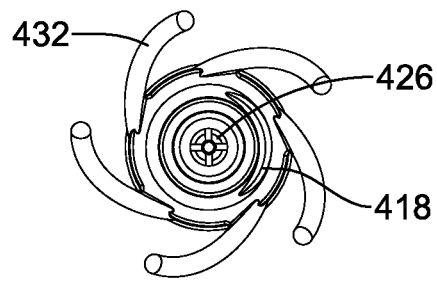
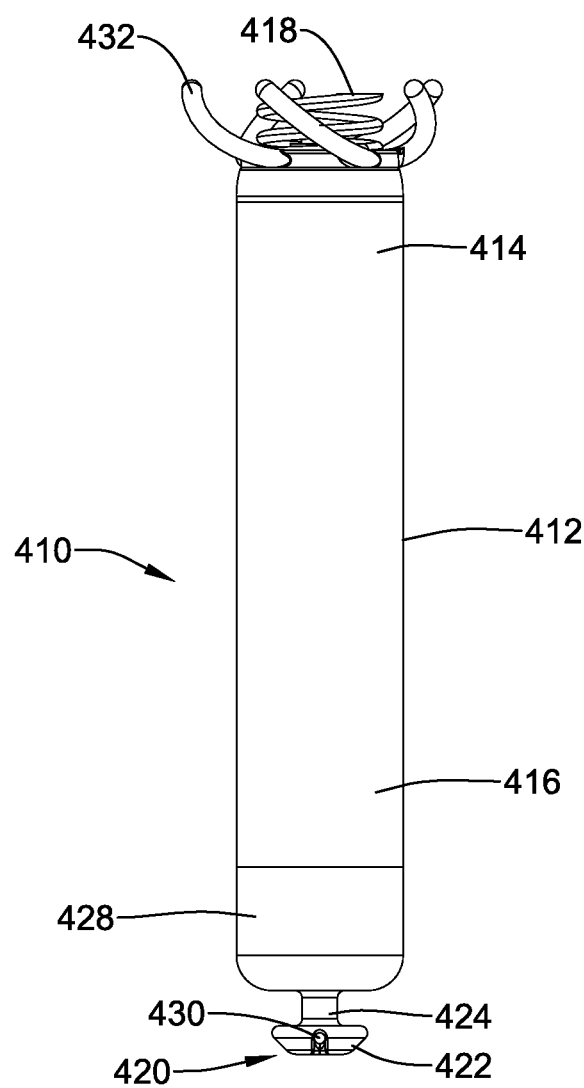
FIG. 6

LEADLESS CARDIAC PACING DEVICES

CROSS-REFERENCES TO RELATED APPLICATIONS

This application claims the benefit of U.S. Provisional Application No. 61/866,813 filed Aug. 16, 2013, the complete disclosure of which is herein incorporated by reference.

TECHNICAL FIELD

The present disclosure pertains to medical devices, and methods for manufacturing medical devices. More particularly, the present disclosure pertains to leadless cardiac pacing devices.

BACKGROUND

A wide variety of medical devices have been developed for medical use, for example, cardiac use. Some of these devices include catheters, leads, pacemakers, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example implantable leadless pacing device may include a pacing capsule. The pacing capsule may include a housing. The housing may have a proximal region and a distal region. A first electrode may be disposed along the distal region. An anchoring member may be coupled to the distal region. One or more anti-rotation members may be fixedly attached to the distal region.

An example implantable leadless pacing device system may include a delivery catheter having a proximal section, a distal holding section, and a lumen formed therein. A push member may be slidably disposed within the lumen. A leadless pacing device may be slidably received within the distal holding section. The leadless pacing device may include a housing having a proximal region and a distal region. A first electrode may be disposed along the distal region. An anchoring member may be coupled to the distal region. One or more anti-rotation members may be fixedly attached to the distal region.

Another example implantable leadless pacing device system may include a delivery catheter having a proximal section, a distal holding section, and a lumen formed therein. A push member may be slidably disposed within the lumen. A leadless pacing device may be slidably received within the distal holding section. The leadless pacing device may include a housing having a proximal region and a distal region. A first electrode may be disposed along the distal region. A helical anchoring member may be coupled to the distal region. A plurality of anti-rotation members may be fixedly attached to the distal region and may be spaced from the helical anchoring member.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 2 is a side view of an example leadless pacing device;

FIG. 2A is a distal end view of the example leadless pacing device shown in FIG. 2;

FIG. 2B is a proximal end view of the example leadless pacing device shown in FIG. 2;

FIG. 3 is a side view of another example leadless pacing device;

FIG. 3A is a distal end view of the example leadless pacing device shown in FIG. 3;

FIG. 4 is a side view of another example leadless pacing device;

FIG. 4A is a distal end view of the example leadless pacing device shown in FIG. 4;

FIG. 5 is a side view of another example leadless pacing device;

FIG. 5A is a distal end view of the example leadless pacing device shown in FIG. 5;

FIG. 5B is a cross-sectional view taken through line 5B-5B of FIG. 5;

FIG. 6 is a side view of another example leadless pacing device;

FIG. 6A is a distal end view of the example leadless pacing device shown in FIG. 6;

Figure 1:
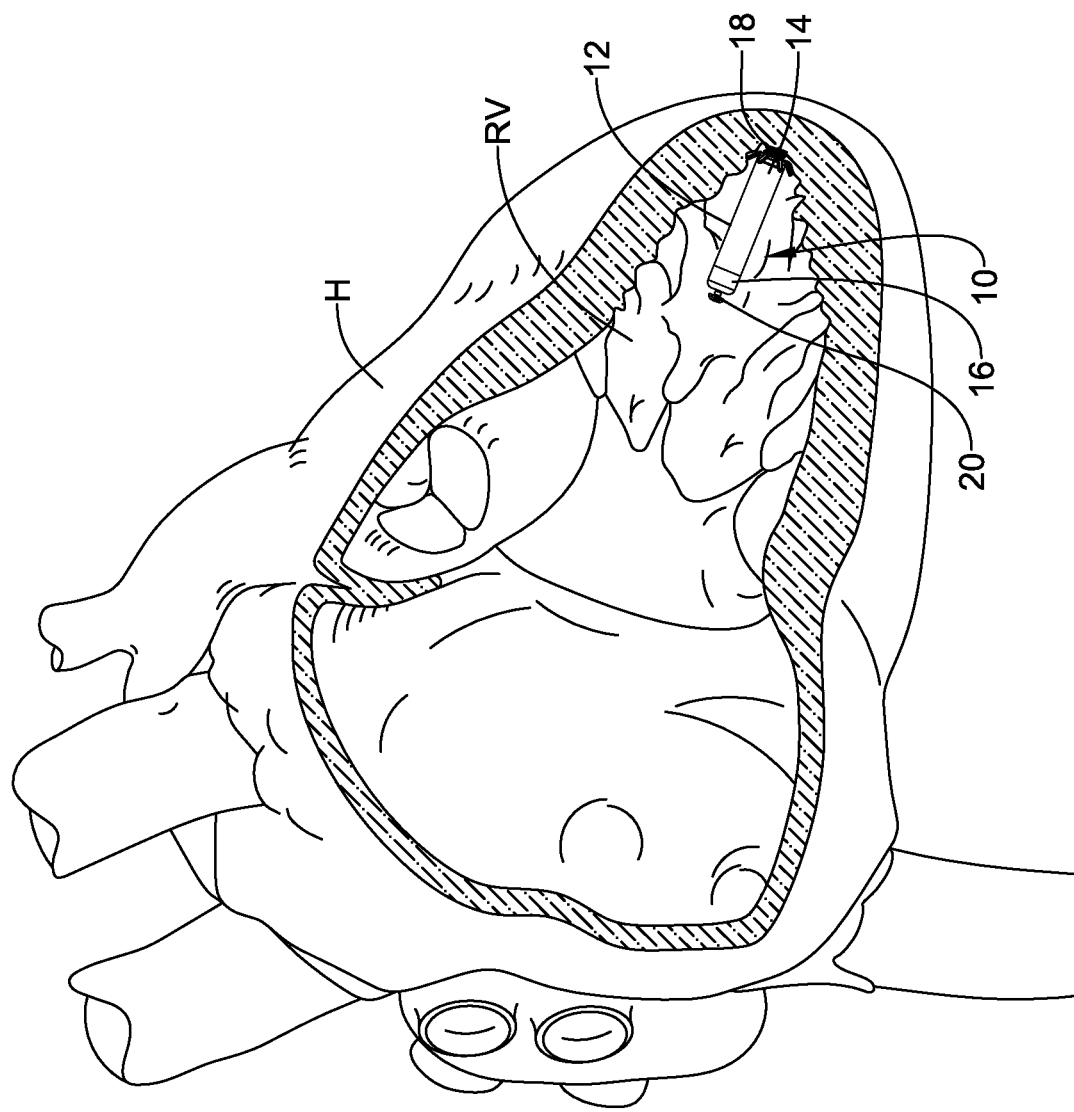
FIG. 1 is a plan view of an example leadless pacing device implanted within a heart.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. A leadless cardiac pacemaker may take the form of a relatively small capsule that may be fixed to an intracardiac implant site in a cardiac chamber. It can be readily appreciated that the implantation of a leadless pacing device within a beating heart could become dislodged as the heart functions. Accordingly, it may be desirable for a leadless pacing device to include an anchoring mechanism and/or one or more anchoring members to help securing the pacing device to the heart.

FIG. 1 illustrates an example implantable leadless cardiac pacing device 10 implanted in a chamber of a heart H such as, for example, the right ventricle RV. Device 10 may include a shell or housing 12 having a distal region 14 and a proximal region 16. One or more anchoring members 18 may be disposed adjacent to distal region 14. Anchoring member 18 may be used to attach device 10 to a tissue wall of the heart H, or otherwise anchor implantable device 10 to the anatomy of the patient. A docking member 20 may be disposed adjacent to proximal region 16 of housing 12. Docking member 20 may be utilized to facilitate delivery and/or retrieval of implantable device 10.

Some of the features of device 10 can be seen in FIG. 2, FIG. 2A, and FIG. 2B. For example, device 10 may include a first electrode 26 positioned adjacent to the distal region 14 of the housing 12. A second electrode 28 may also be defined along housing 12. For example, housing 12 may include a conductive material and may be insulated along a portion of its length. A section along proximal region 16 may be free of insulation so as to define second electrode 28. Electrodes 26/28 may be sensing and/or pacing electrodes to provide electro-therapy and/or sensing capabilities. First electrode 26 may be capable of being positioned against or otherwise contact the cardiac tissue of the heart H while second electrode 28 may be spaced away from the first electrode 26, and thus spaced away from the cardiac tissue. Device 10 may also include a pulse generator (e.g., electrical circuitry) and a power source (e.g., a battery) within housing 12 to provide electrical signals to electrodes 26/28. Electrical communication between pulse generator and electrodes 26/28 may provide electrical stimulation to heart tissue and/or sense a physiological condition.

Docking member 20 may include a head portion 22 and a neck portion 24 extending between housing 12 and head portion 22. Head portion 22 may be capable of engaging with a delivery and/or retrieval catheter. For example, head portion 22 may include a bore or opening 30 formed therein. The ends of bore 30 may be open or exposed while a central region of bore 30 may be covered by a section 34 of head portion. During delivery, device 10 may be secured to a delivery device by extending a suture through bore 30. A portion of the delivery catheter may include projections or lugs that may engage bore 30. Some additional details of example delivery devices for delivering device 10 to cardiac tissue are disclosed herein.

Docking member 20 may also be engaged if it is desired to retrieve and/or reposition device 10. For example, a retrieval catheter may be advanced to a position adjacent to device 10. A retrieval mechanism such as a snare, tether, arm, or other suitable structure may extend from the retrieval catheter and engage head portion 22. When suitably engaged, device 10 may be pulled from the cardiac tissue and, ultimately, removed from the patient or repositioned.

As the name suggest, anchoring member 18 may be used to anchor device 10 to the target tissue. A suitable number of anchoring member 18 may be used with device 10. For example, device 10 may include one, two, three, four, five, six, seven, eight, or more anchoring members. In at least some embodiments, anchoring member 18 may take the form of a helix or screw. According to these embodiments, anchoring member 18 may be threaded into cardiac tissue. Some additional details of example mechanisms for threading/anchoring device 10 to cardiac tissue are disclosed herein.

Figure 2C:
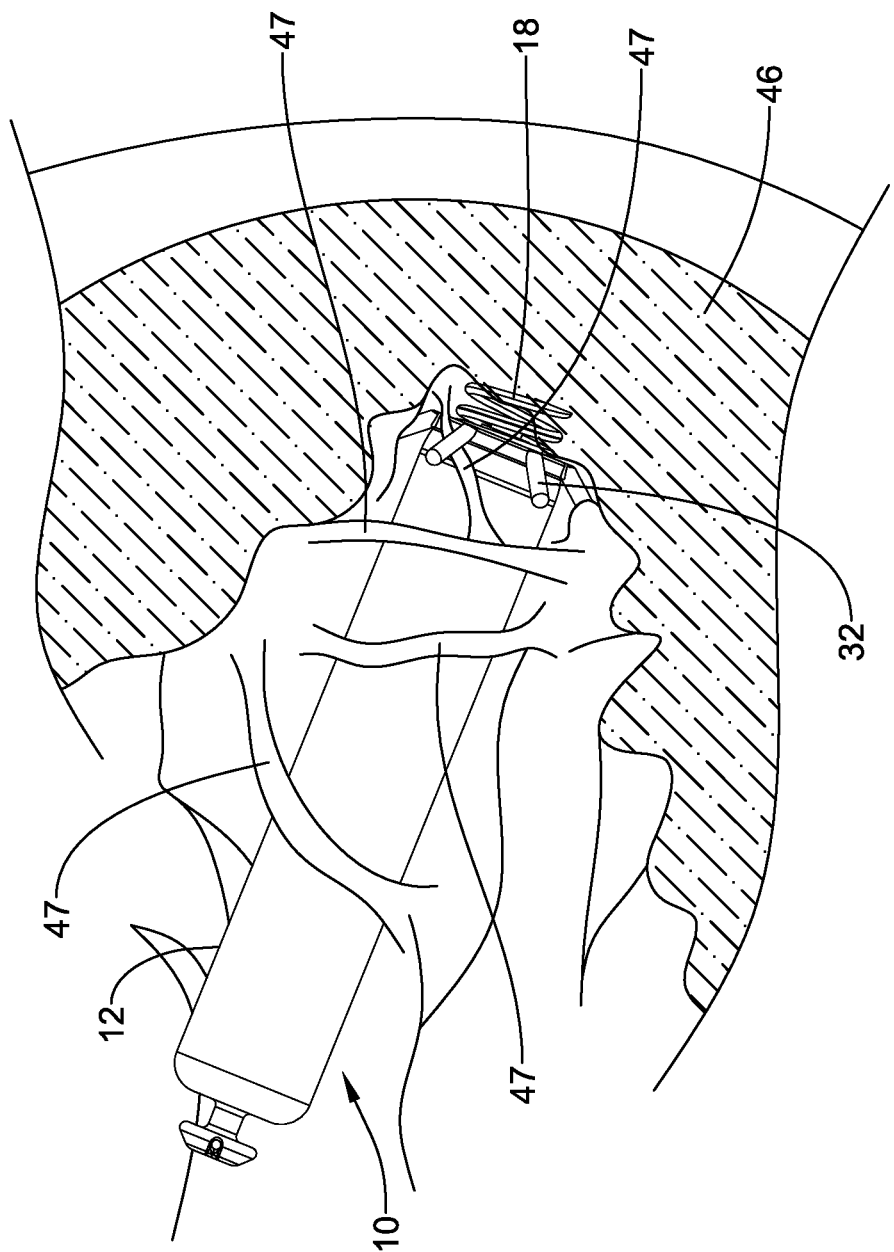
FIG. 2C is a plan view of the example leadless pacing device shown in FIG. 2 implanted within a cardiac tissue.

It can be appreciated that in order to securely anchor device 10 to cardiac tissue with a helical anchoring member 18, it may be desirable to reduce or prevent unintended rotation and/or "unthreading" of device 10. Because of this device, device 10 may include one or more anti-rotation tines or members 32. In general, anti-rotation members 32 may be disposed along distal region 14 and may extend radially outward from housing 12. In at least some embodiments, anti-rotation members 32 may help to maintain device 10 in a securely anchored arrangement. For example, FIG. 2C illustrates device 10 implanted within a cardiac tissue 46. In this example, cardiac tissue 46 may have a number of trabeculae 47 along the surface thereof. Anti-rotation members 32 may become entwined with trabeculae 47 so that unwanted rotation of device 10 may be reduced and/or prevented.

Anti-rotation members 32 may be fixedly attached to housing 12. In other words, anti-rotation members may be designed so that during typical use, anti-rotation members 32 remain attached to housing 12. In some embodiments, anti-rotation member 32 may have some freedom of movement relative to housing 10. For example, anti-rotation members 32 may be capable of pivoting, rotating, or otherwise moving relative to housing 12.

The form of anti-rotation members 32 may vary. For example, anti-rotation members 32 may take the form of cylindrical rods or tubes projecting from housing 12. The rods may have a generally circular cross-sectional shape. In at least some embodiments, anti-rotation members 32 may be substantially straight. In other embodiments, anti-rotation members 32 may include one or more curves or bends. A variety of other shapes, forms, and configurations are also contemplated for anti-rotation members 32 and some of these are disclosed herein. In addition, some devices may include combinations of differently shaped or oriented anti-rotation members 32.

FIG. 3 and FIG. 3A illustrate another example implantable leadless cardiac pacing device 110 similar in form and function to other devices disclosed herein. For example, device 110 may include housing 112 with distal region 114 and proximal region 116. Anchoring member 118 may be disposed along distal region 114. Device may also include electrodes 126/128 and docking member 120. Docking member 120 may include head region 122 and neck region 124. Bore 130 may be formed in head region 122.

Device 110 may include anti-rotation members 132. According to this embodiment, anti-rotation members 132 may be relatively flattened relative to anti-rotation members 132 or otherwise have a ribbon-like shape. In cross-section, anti-rotation members 132 may be described as having a rectangular cross-sectional shape. This is just an example. Other shapes are contemplated. Just like other anti-rotation members disclosed, anti-rotation members 132 herein may be capable of reducing or preventing unwanted rotation of device 110. For example, anti-rotation members 132 may become engaged or otherwise entwined with trabeculae along the inner walls of the heart so that unwanted rotation of device 110 may be reduced and/or prevented.

FIG. 4 and FIG. 4A illustrate another example implantable leadless cardiac pacing device 210 similar in form and function to other devices disclosed herein. For example, device 210 may include housing 212 with distal region 214 and proximal region 216. Anchoring member 218 may be disposed along distal region 214. Device may also include electrodes 226/228 and docking member 220. Docking member 220 may include head region 222 and neck region 224. Bore 230 may be formed in head region 222.

Device 210 may include anti-rotation members 232. According to this embodiment, anti-rotation members 232 may extend "straight" radially outward from distal region 214. For example, in at least some embodiments anti-rotation members 232 may extend in a direction that is substantially perpendicular to the longitudinal axis of housing 212. In other words, anti-rotation members 232 may lie in a plane that is normal to the longitudinal axis of housing 212. Just like other anti-rotation members disclosed, anti-rotation members 232 herein may be capable of reducing or preventing unwanted rotation of device 210. For example, anti-rotation members 232 may become engaged or otherwise entwined with trabeculae along the inner walls of the heart so that unwanted rotation of device 210 may be reduced and/or prevented.

FIG. 5, FIG. 5A, and FIG. 5B illustrate another example implantable leadless cardiac pacing device 310 similar in form and function to other devices disclosed herein. For example, device 310 may include housing 312 with distal region 314 and proximal region 316. Anchoring member 318 may be disposed along distal region 314. Device may also include electrodes 326/328 and docking member 320. Docking member 320 may include head region 322 and neck region 324. Bore 330 may be formed in head region 322.

Device 310 may include anti-rotation members 332. According to this embodiment, anti-rotation members 332 may have a polygonal cross-sectional shape. For example, anti-rotation members 332 may have a substantially trapezoidal cross-sectional shape. This is just an example. Other shapes are contemplated. Just like other anti-rotation members disclosed, anti-rotation members 332 herein may be capable of reducing or preventing unwanted rotation of device 310. For example, anti-rotation members 332 may become engaged or otherwise entwined with trabeculae along the inner walls of the heart so that unwanted rotation of device 310 may be reduced and/or prevented.

FIG. 6 and FIG. 6A illustrate another example implantable leadless cardiac pacing device 410 similar in form and function to other devices disclosed herein. For example, device 410 may include housing 412 with distal region 414 and proximal region 416. Anchoring member 418 may be disposed along distal region 414. Device may also include electrodes 426/428 and docking member 420. Docking member 420 may include head region 422 and neck region 424. Bore 430 may be formed in head region 422.

Device 410 may include anti-rotation members 432. According to this embodiment, anti-rotation members 432 may be angled and/or curved. For example, anti-rotation members 432 may extend circumferentially about housing 412 and may also curve and extend in the distal direction. This orientation of anti-rotation members 432 may be described as being helical or helically-oriented. This is just an example. Other shapes are contemplated. Just like other anti-rotation members disclosed, anti-rotation members 432 herein may be capable of reducing or preventing unwanted rotation of device 410. For example, anti-rotation members 432 may become engaged or otherwise entwined with trabeculae along the inner walls of the heart so that unwanted rotation of device 410 may be reduced and/or prevented.

Figure 7A:
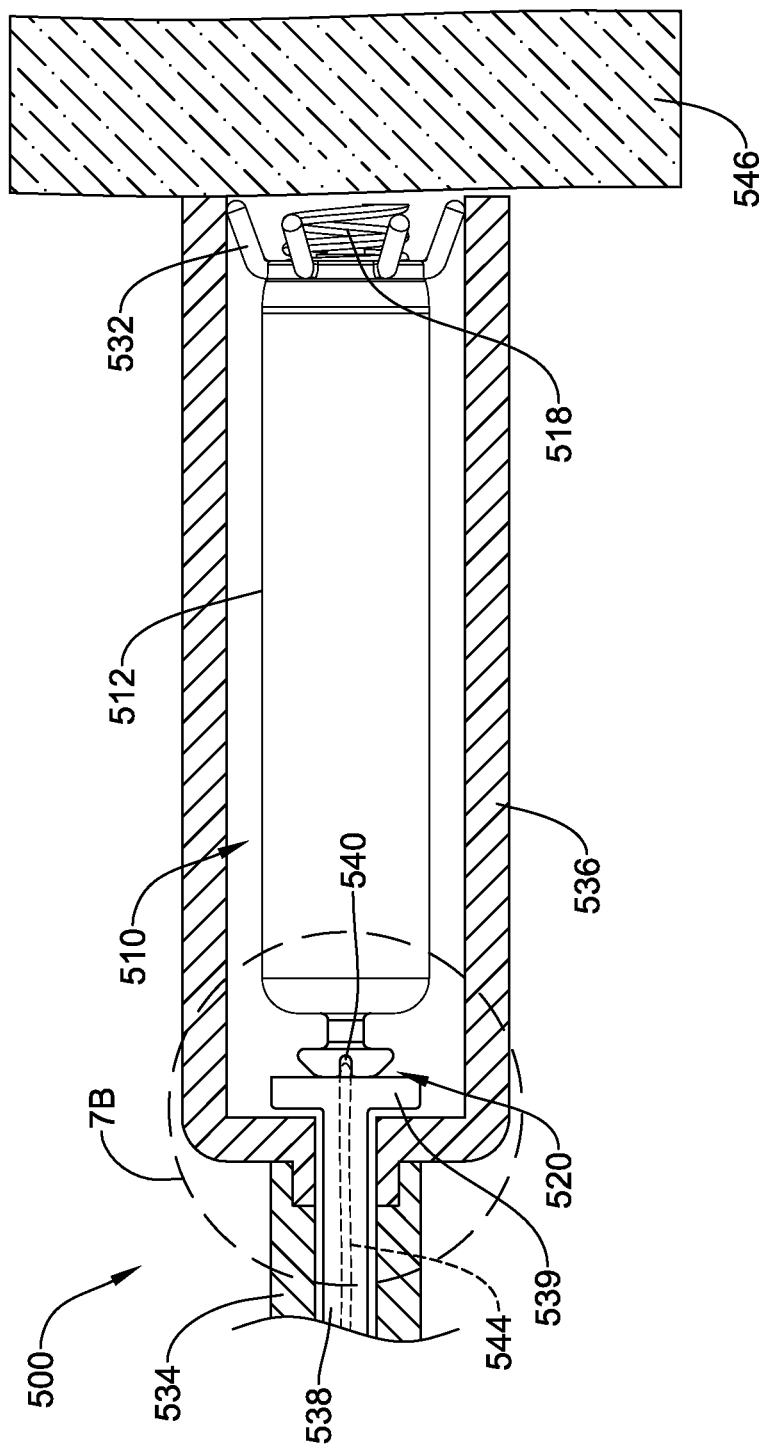
FIG. 7A is a partial cross-sectional side view of an example medical device system positioned adjacent to a cardiac tissue.
Figure 7B:
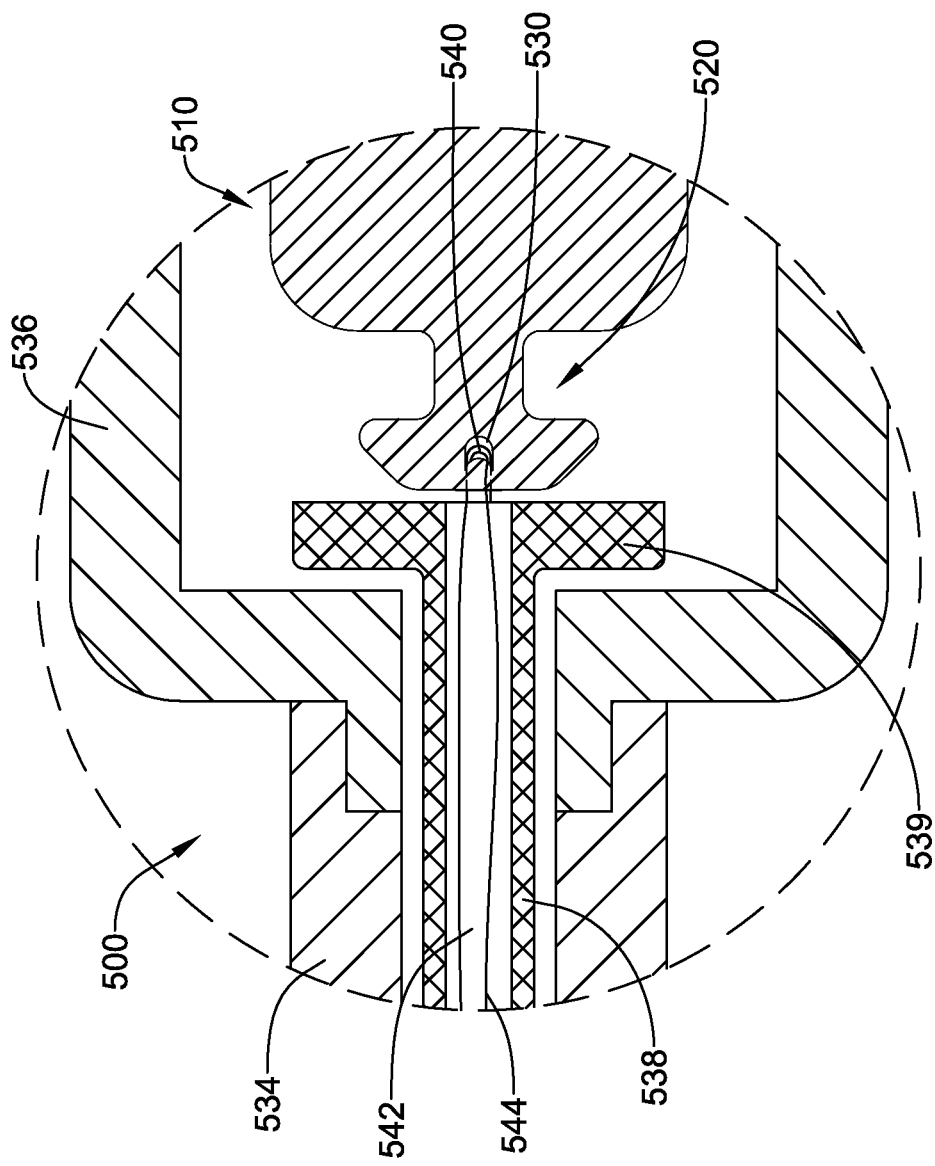
FIG. 7B is an enlarged view of a portion of the example medical device system shown in FIG. 7A.
Figure 7C:
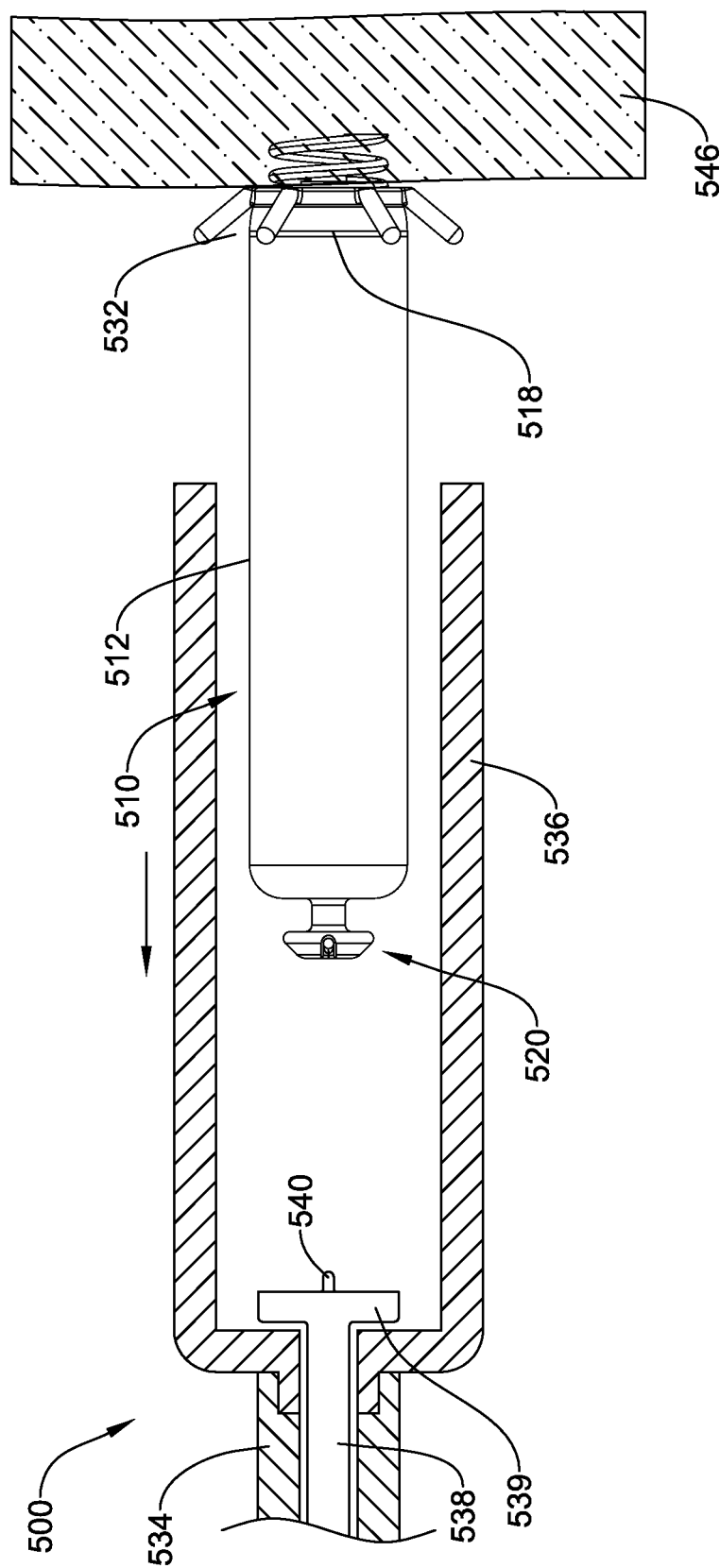
FIG. 7C is a partial cross-sectional side view of the example medical device system shown in FIG. 7A with a leadless pacing device implanted within a cardiac tissue.

FIGS. 7A-7C illustrates a delivery catheter 500 that may be used, for example, to deliver implantable leadless cardiac pacing device 510 (which may be similar in form and function to other implantable leadless cardiac pacing devices disclosed herein) to a suitable location within the anatomy (e.g., the heart). Catheter 500 may include a proximal member or region 534 and a distal member or holding section 536. A push member 538 may be disposed (e.g., slidably disposed) within proximal region 534. A distal or head region 539 of push member 142 may be disposed within distal holding section 536. Head region 539 may be capable of engaging docking member 520 of device 510. For example, head region 539 may include one or more lugs 540 that are capable of engaging bore 530 formed in docking member 520. When lugs 540 are engaged with bore 530, push member 538 may be rotated to thread anchor member 518 into a target region 546 (e.g., a region of the heart such as the right ventricle) as shown in FIG. 7C. In some embodiments, a holding member or suture 544 may also extend through a lumen 542 formed in push member 538 and pass through bore 530 so as to secure push member 538 to device 510 during portions or all of the delivery process.

Catheter 500 may be advanced through the vasculature to target region 546. For example, catheter 500 may be advanced through a femoral vein, into the inferior vena cava, into the right atrium, through the tricuspid valve, and into the right ventricle. Target region 546 may be a portion of the right ventricle. For example, target region 546 may be a portion of the right ventricle near the apex of the heart.

Device 510 may include anchor member 518 and anti-rotation members 532. Just like other anti-rotation members disclosed, anti-rotation members 532 herein may be capable of reducing or preventing unwanted rotation of device 510. For example, anti-rotation members 532 may become engaged or otherwise entwined with trabeculae along the inner walls of the heart so that unwanted rotation of device 510 may be reduced and/or prevented.

Figure 8:
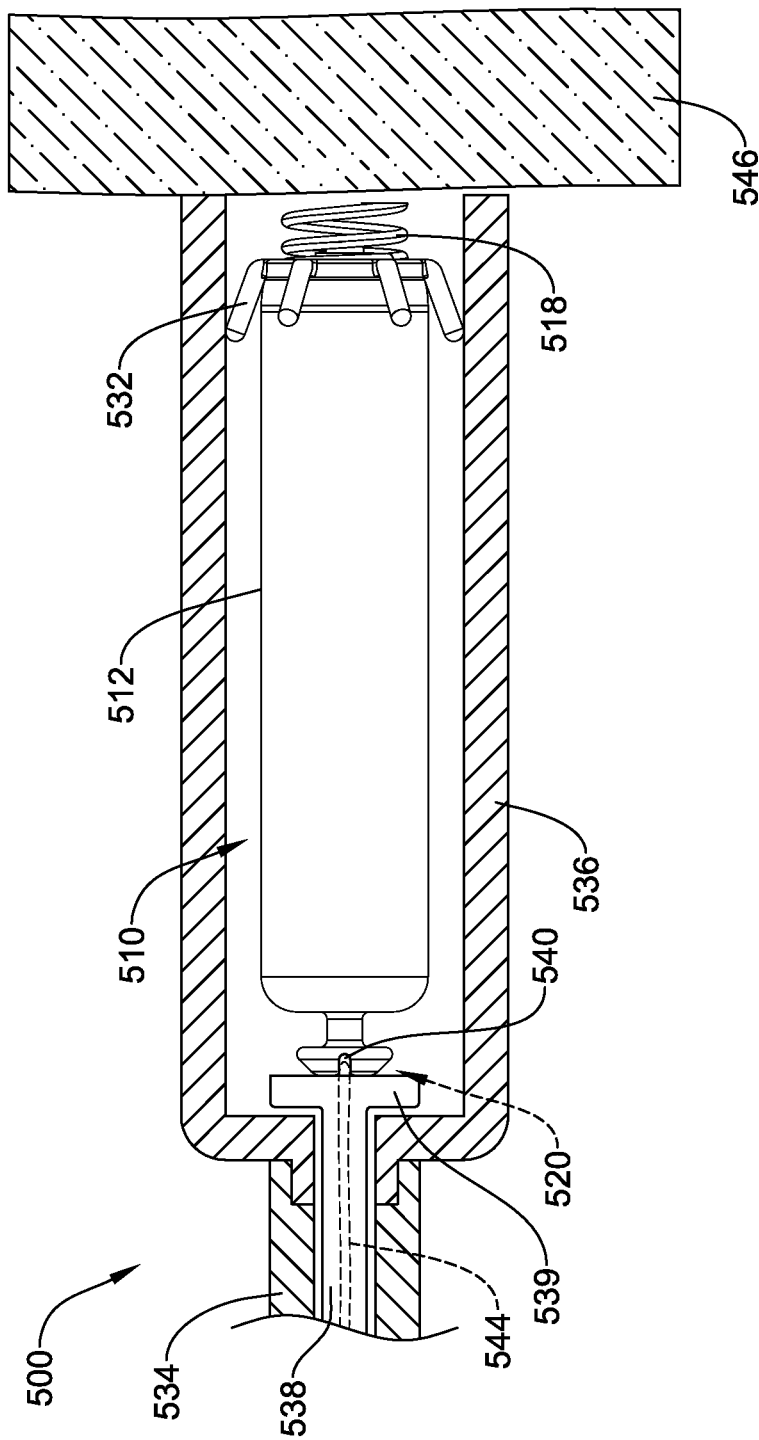
FIG. 8 is a partial cross-sectional side view of an example medical device system positioned adjacent to a cardiac tissue.

During advancement of catheter 500 through the vasculature, anti-rotation members 532 may be oriented in the distal direction (e.g., toward the distal end of device 510 and/or distally from device 510). Anti-rotation member 532 may be pivotable along device 510 so that anti-rotation members 532 are capable of pivoting so as to become oriented in the proximal direction after implantation. Such an orientation may aid anti-rotation members 532 in becoming engaged with trabeculae. However, other orientations are also contemplated. For example, FIG. 8A shows device 510 with anti-rotation members 532 oriented in the proximal direction (e.g., toward the proximal end of device 510) during delivery. After implantation, anti-rotation members 532 may remain oriented in the proximal direction (e.g., as shown in FIG. 7C).

The materials that can be used for the various components of device 10 and catheter 500 (and/or other devices/catheters disclosed herein) may include those commonly associated with medical devices. For example, device 10 and/or catheter 500 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of device 10 and/or catheter 500 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of device 10 and/or catheter 500 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of device 10 and/or catheter 500 to achieve the same result.

In some embodiments, a degree of Magnetic Resonance Imaging (MRI) compatibility is imparted into device 10 and/or catheter 500. For example, device 10 and/or catheter 500 (or portions thereof) may be made of a material that does not substantially distort the image and create substantial artifacts (i.e., gaps in the image). Certain ferromagnetic materials, for example, may not be suitable because they may create artifacts in an MRI image. Device 10 and/or catheter 500 (or portions thereof) may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An implantable leadless pacing device, comprising: a pacing capsule including a cylindrical housing, the cylindrical housing having a proximal end, a proximal region extending to the proximal end, a distal end, a distal region extending to the distal end, a central longitudinal axis extending through the proximal and distal ends, and a circumferential surface extending longitudinally between the proximal region and the distal region and surrounding the central longitudinal axis;
 a first electrode disposed along the distal region;
 an anchoring member coupled to the distal region, wherein the anchoring member includes a helical screw extending through greater than 360 degrees of rotation; and
 a plurality of anti-rotation members fixedly attached to the distal region and arranged circumferentially around the helical screw, the plurality of anti-rotation members extending radially outward beyond the circumferential surface adapted to engage a wall of a heart or otherwise entwine with trabeculae of the heart, and
 wherein the plurality of anti-rotation members have distal ends which extend distal of a distal extent of the helical screw when in an unconstrained configuration;
 wherein the first electrode is disposed radially within and spaced apart from the helical screw.

2. The implantable leadless pacing device of claim 1, wherein at least some of the plurality of anti-rotation members include a curved region.

3. The implantable leadless pacing device of claim 1, wherein at least some of the plurality of anti-rotation members have a substantially circular cross-sectional shape.

4. The implantable leadless pacing device of claim 1, wherein at least some of the plurality of anti-rotation members have a polygonal cross-sectional shape.

5. The implantable leadless pacing device of claim 1, wherein at least some of the plurality of anti-rotation members are capable of pivoting relative to the housing.

6. An implantable leadless pacing device system, the system comprising:
 a delivery catheter having a proximal section, a distal holding section, and a lumen formed therein;
 a push member slidably disposed within the lumen;
 a leadless pacing device slidably received within the distal holding section, the leadless pacing device comprising:
  a housing having a proximal end, a proximal region extending to the proximal end, a distal end, a distal region extending to the distal end, a longitudinal axis extending through the proximal and distal ends, and a peripheral surface extending longitudinally between the proximal region and the distal region and surrounding the longitudinal axis,
  a first electrode disposed along the distal region,
  an anchoring member coupled to the distal region, and
  one or more anti-rotation members fixedly attached to the distal region and extending radially outward beyond the peripheral surface of the housing in an unconstrained configuration,
  wherein the one or more anti-rotation members each has a distal end which extends distal of a distal extent of the anchoring member when in the unconstrained configuration,
  wherein each of the one or more anti-rotation members is engaged with an inner surface of the distal holding section and moved away from the unconstrained configuration into a constrained configuration oriented in a distal direction for advancement of the delivery catheter;
  wherein the first electrode is disposed radially within and spaced apart from the anchoring member.

7. The system of claim 6, wherein a docking member is coupled to the proximal region of the housing, the docking member being adapted to operably engage the push member.

8. The system of claim 7, wherein the push member is capable of rotating the housing when the push member is engaged with the docking member.

9. The system of claim 6, wherein at least some of the one or more anti-rotation members include a curved region.

10. The system of claim 6, wherein at least some of the one or more anti-rotation members are capable of pivoting relative to the housing.

11. The system of claim 6, wherein the anchoring member includes a helical screw extending through greater than 360 degrees of rotation.

12. An implantable leadless pacing device, comprising:
   a pacing capsule including a housing, the housing having a proximal end, a proximal region extending to the proximal end, a distal end, a distal region extending to the distal end, a central longitudinal axis extending through the proximal and distal ends, and a peripheral surface extending longitudinally between the proximal region and the distal region and surrounding the central longitudinal axis, the peripheral surface located at a first distance away from the central longitudinal axis, the first distance measured perpendicular to the central longitudinal axis;
   a first electrode disposed along the distal region;
   an anchoring member coupled to the distal region, wherein the anchoring member includes a helical screw; and
   a plurality of anti-rotation members fixedly attached to the distal region and adapted to engage a wall of a heart or otherwise entwine with trabeculae of the heart,
   wherein the plurality of anti-rotation members are circumferentially arranged around the helical screw and extend radially outward of the helical screw and beyond the peripheral surface of the housing,
   wherein in an unconstrained state, each of the plurality of anti-rotation members is configured to have a distal end which extends distal of a distal extent of the helical screw; and
   wherein in the unconstrained state, the distal end of each of the plurality of anti-rotation members is positioned at a second distance away from the central longitudinal axis, the second distance measured perpendicular to the central longitudinal axis, wherein the second distance is greater than the first distance;
   wherein the helical screw is disposed circumferentially around the first electrode and spaced therefrom.

13. The implantable leadless pacing device of claim 12, wherein the helical screw extends through greater than 360 degrees of rotation.

14. The implantable leadless pacing device of claim 12, wherein each of the plurality of anti-rotation members has a base that is fixedly attached to the distal region and are capable of pivoting about the base to move the anti-rotation member relative to the housing.

15. The implantable leadless pacing device of claim 12, wherein the peripheral surface is a cylindrical surface.

16. The implantable leadless pacing device of claim 12, wherein the helical screw extends through at least 720 degrees of rotation.

* * * * *